US012678274B2

(12) United States Patent
Hagiwara et al.

(10) Patent No.: US 12,678,274 B2
(45) Date of Patent: Jul. 14, 2026

(54) BLOOD VESSEL COVER

(71) Applicant: Akeo Hagiwara, Otsu (JP)

(72) Inventors: Akeo Hagiwara, Otsu (JP); Yosaku Hagiwara, Osaka (JP)

(73) Assignee: Akeo Hagiwara, Otsu (JP)

( * ) Notice: Subject to any disclaimer, the term of this patent is extended or adjusted under 35 U.S.C. 154(b) by 367 days.

(21) Appl. No.: 18/689,272

(22) PCT Filed: Aug. 22, 2022

(86) PCT No.: PCT/JP2022/031604
§ 371 (c)(1),
(2) Date: Mar. 5, 2024

(87) PCT Pub. No.: WO2023/037859
PCT Pub. Date: Mar. 16, 2023

(65) Prior Publication Data
US 2024/0366362 A1 Nov. 7, 2024

(30) Foreign Application Priority Data

Sep. 8, 2021 (JP) ................................. 2021-146520

(51) Int. Cl.
*A61F 2/06* (2013.01)
(52) U.S. Cl.
CPC ........ *A61F 2/06* (2013.01); *A61F 2230/0069* (2013.01); *A61F 2250/0018* (2013.01)
(58) Field of Classification Search
CPC ............................. A61F 2/06; A61F 2002/068
See application file for complete search history.

(56) References Cited

U.S. PATENT DOCUMENTS

| | | | |
|---|---|---|---|
| 6,019,788 A | 2/2000 | Butters et al. | |
| 10,076,431 B2 * | 9/2018 | Sirhan | ...................... A61F 2/89 |
| 2004/0215309 A1 | 10/2004 | Moritz et al. | |

(Continued)

FOREIGN PATENT DOCUMENTS

| | | |
|---|---|---|
| JP | 2004-535896 A | 12/2004 |
| JP | 2008-522735 A | 7/2008 |

(Continued)

OTHER PUBLICATIONS

"Machinery equipment 7 Visceral function substitutes Highly controlled medical device Artificial blood vessel using collagen", JMDN code: 35093204, Meadix Hemashield Knit Graft, 2021, Total 12 pages.

(Continued)

*Primary Examiner* — Kevin T Truong
(74) *Attorney, Agent, or Firm* — Birch, Stewart, Kolasch & Birch, LLP

(57) ABSTRACT

Disclosed is a blood vessel cover that can reduce or prevent intimal thickening by remodeling the vein into a buffer system vessel.
A cylindrical blood vessel cover (10) is continuous around the entire circumference and to be placed on an outer circumference of a vein (4) that is anastomosed to an artery (3) or to an artificial blood vessel, the blood vessel cover (10) has a portion (A), and the portion (A) has a 20% elastic index of 1.2 N or less when an inner diameter of the blood vessel cover (10) is expanded in a radial direction by 20% from its natural state.

12 Claims, 5 Drawing Sheets

(56)          References Cited

U.S. PATENT DOCUMENTS

| | | | |
|---|---|---|---|
| 2008/0118561 A1 | 5/2008 | Nugent et al. | |
| 2008/0119946 A1 | 5/2008 | Nugent et al. | |
| 2008/0125858 A1 | 5/2008 | Edelman et al. | |
| 2008/0160532 A1 | 7/2008 | Shah et al. | |
| 2008/0208323 A1 | 8/2008 | El-Kurdi et al. | |
| 2009/0035346 A1 | 2/2009 | Nugent et al. | |
| 2010/0204783 A1 | 8/2010 | Nugent et al. | |
| 2010/0240036 A1 | 9/2010 | Shah et al. | |
| 2010/0318016 A1 | 12/2010 | Nugent et al. | |
| 2011/0002973 A1 | 1/2011 | Nugent et al. | |
| 2011/0045054 A1 | 2/2011 | Edelman et al. | |
| 2011/0229549 A1 | 9/2011 | Nugent et al. | |
| 2011/0287422 A1 | 11/2011 | Harris et al. | |
| 2012/0330437 A1 | 12/2012 | El-Kurdi et al. | |
| 2013/0052166 A1 | 2/2013 | Nugent et al. | |
| 2013/0122498 A1 | 5/2013 | Shah et al. | |
| 2013/0210142 A1 | 8/2013 | Nugent et al. | |
| 2014/0087383 A1 | 3/2014 | Shah et al. | |
| 2015/0150673 A1 | 6/2015 | El-Kurdi et al. | |
| 2015/0159227 A1 | 6/2015 | Shah et al. | |
| 2016/0317280 A1 | 11/2016 | El-Kurdi et al. | |
| 2016/0362753 A1 | 12/2016 | Shah et al. | |
| 2017/0340432 A1 | 11/2017 | El-Kurdi et al. | |
| 2018/0289864 A1 | 10/2018 | Hagiwara | |
| 2019/0127809 A1 | 5/2019 | Shah et al. | |
| 2020/0155331 A1* | 5/2020 | Ben-Muvhar | A61F 2/07 |
| 2020/0237494 A1 | 7/2020 | El-Kurdi et al. | |
| 2022/0378576 A1* | 12/2022 | Montoya | A61F 2/94 |
| 2022/0378998 A1 | 12/2022 | Hagiwara | |
| 2022/0409359 A1 | 12/2022 | Hagiwara | |

FOREIGN PATENT DOCUMENTS

| | | | |
|---|---|---|---|
| JP | 2010-516437 | A | 5/2010 |
| JP | 2013-509258 | A | 3/2013 |
| WO | WO 2021-161884 | A1 | 8/2021 |
| WO | WO 2021-177273 | A1 | 9/2021 |

OTHER PUBLICATIONS

Chinese Office Action and Search Report for Chinese Patent Application No. 202180015656.9, dated Feb. 13, 2023, with an English Translation.

Chinese Office Action for Chinese Application No. 202180015656.9, dated Jul. 22, 2023, with an English translation.

Chinese Office Action for Chinese Application No. 202180015656.9, dated Sep. 29, 2023, with an English translation.

Haruguchi, Hiroaki, "I Blood Access Problems associated with blood flow failure", 2000, vol. 15, No. 1, pp. 68-70, Total 9 pages.

International Search Report (PCT/ISA/210) issued in PCT/JP2022/031604, dated Oct. 11, 2022.

International Search Report (PCT/ISA/210) issued in PCT/JP2021/007839, dated Apr. 27, 2021.

Written Opinion of the International Searching Authority (PCT/ISA/237) issued in PCT/JP2022/031604, dated Oct. 11, 2022.

Japanese Office Action for Japanese Application No. 2022-504381, dated Oct. 22, 2024, with English translation.

U.S. Office Action for U.S. Appl. No. 17/899,930, dated Oct. 7, 2024.

* cited by examiner

[FIG. 1]
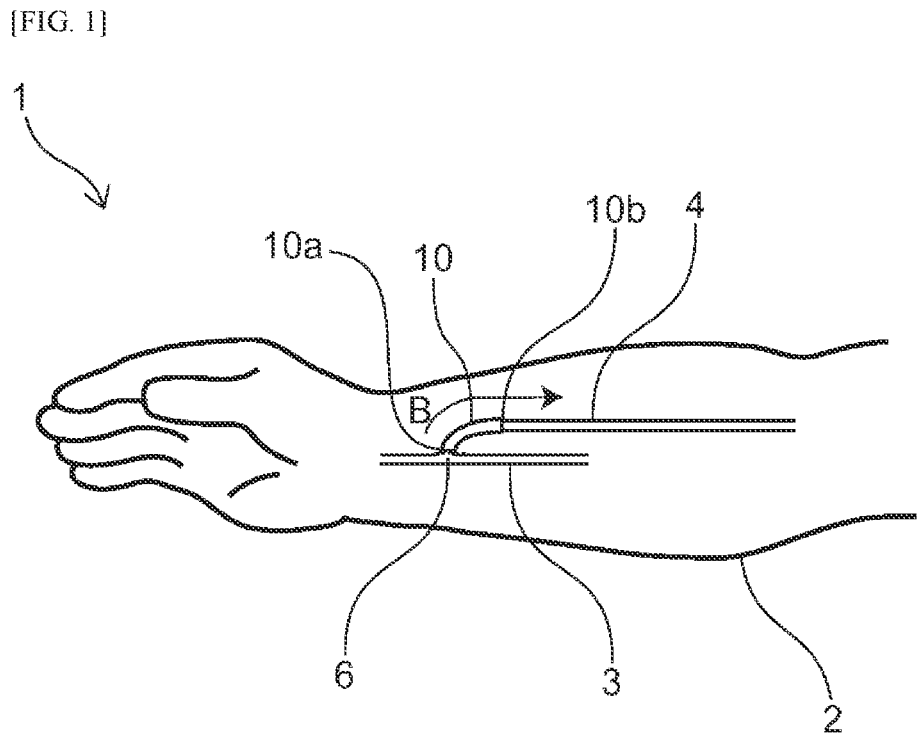
[FIG. 2]
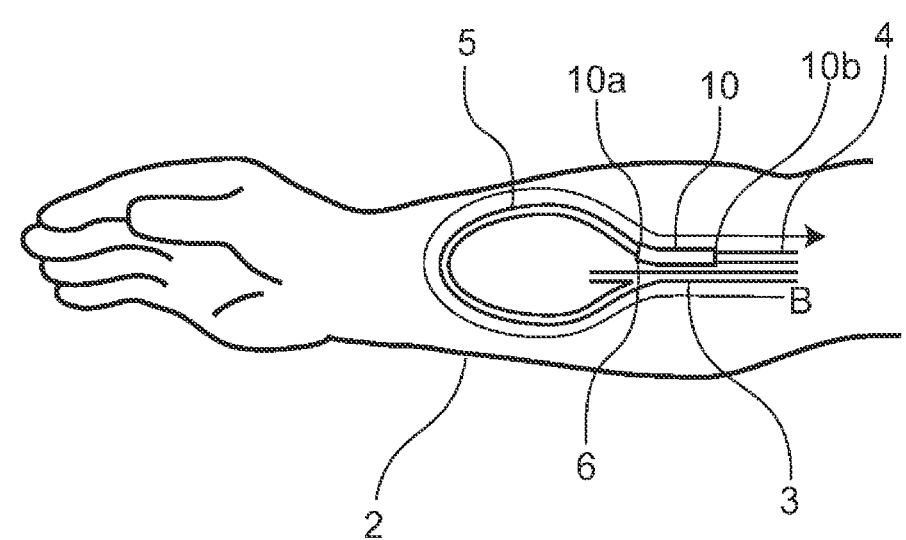

[FIG. 3]
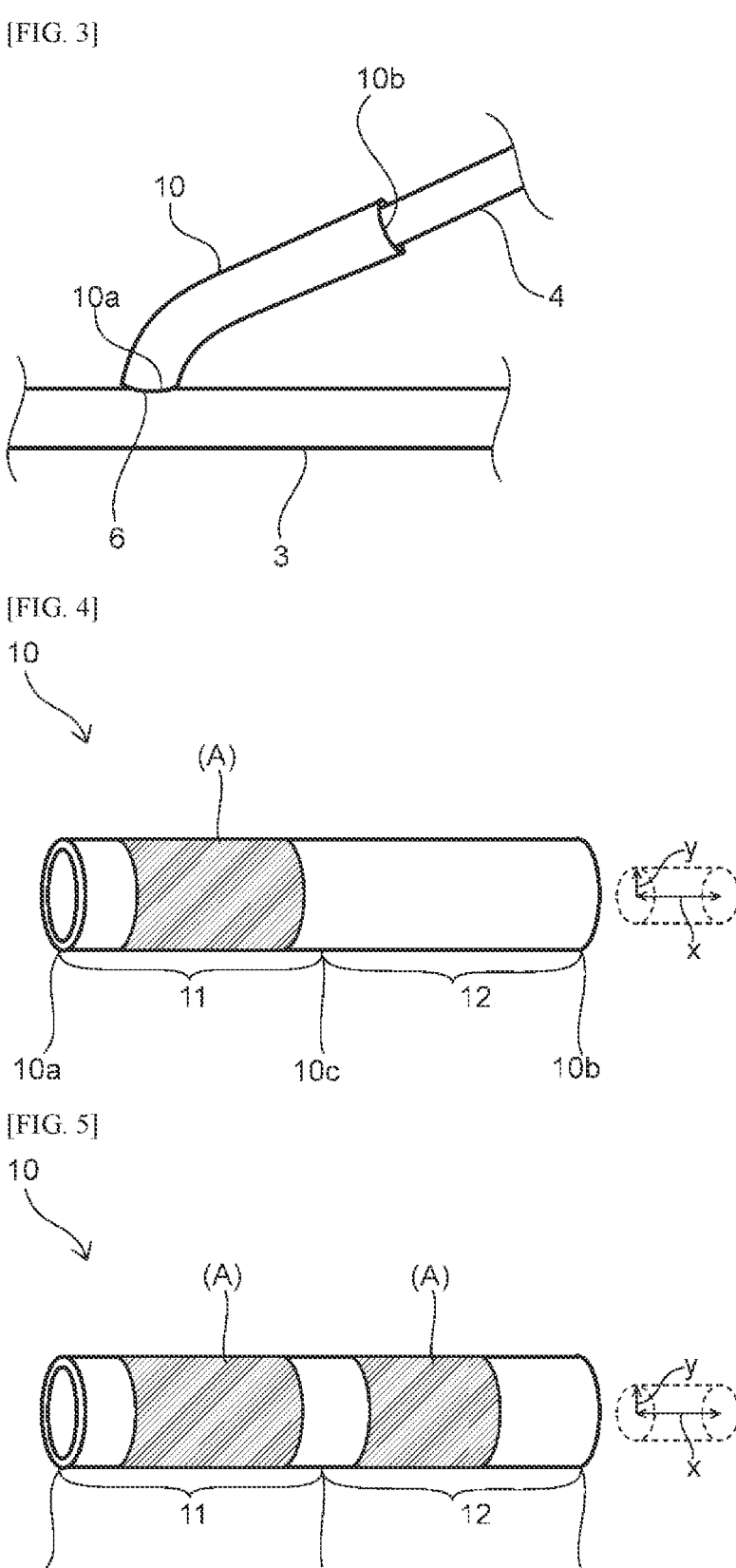
[FIG. 4]
[FIG. 5]

[FIG. 6]
[FIG. 7]
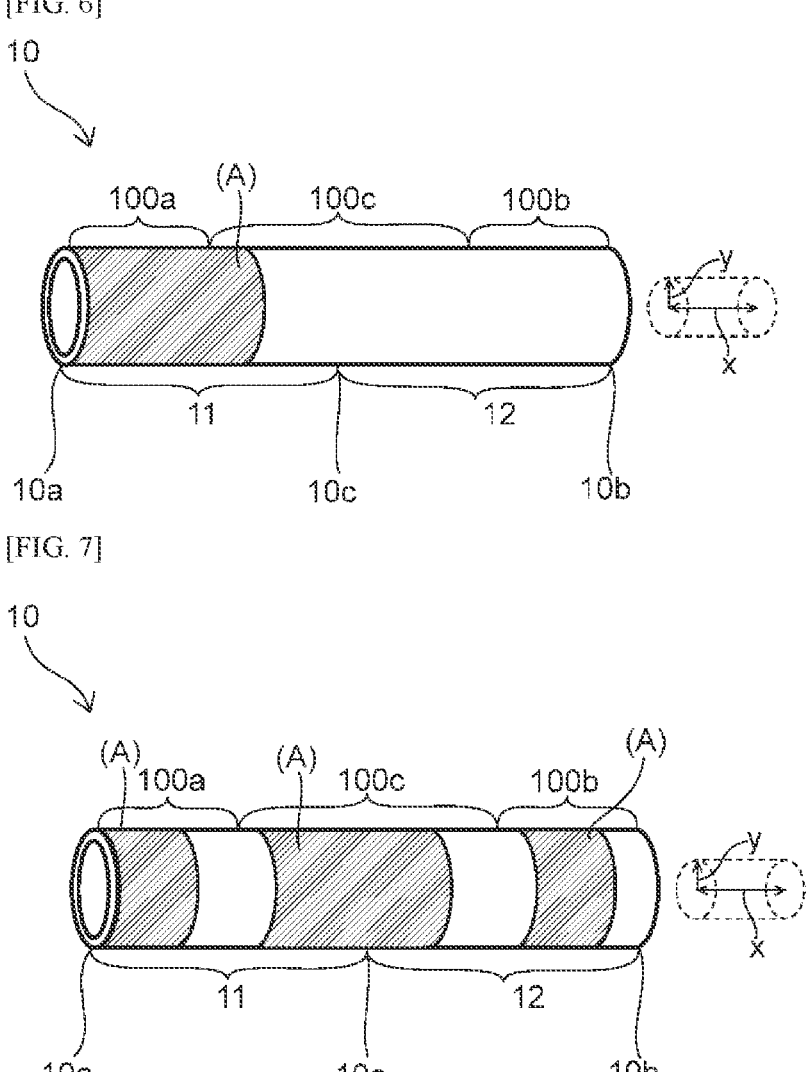

[FIG. 8]
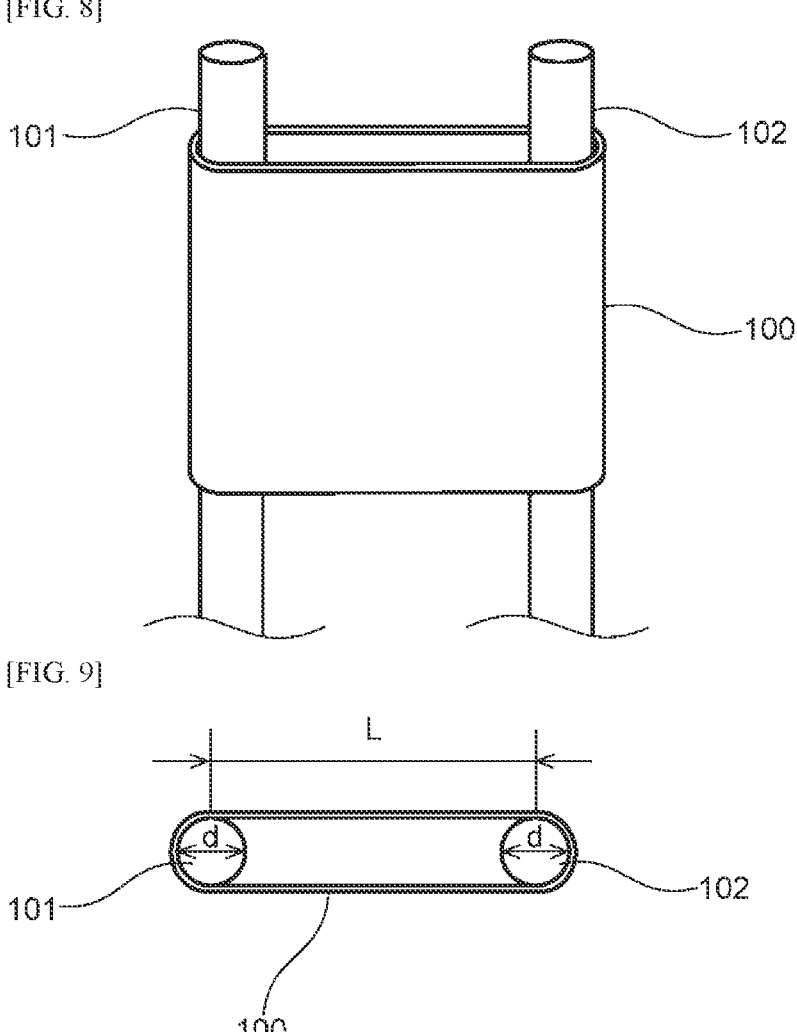
[FIG. 9]

[FIG. 10]
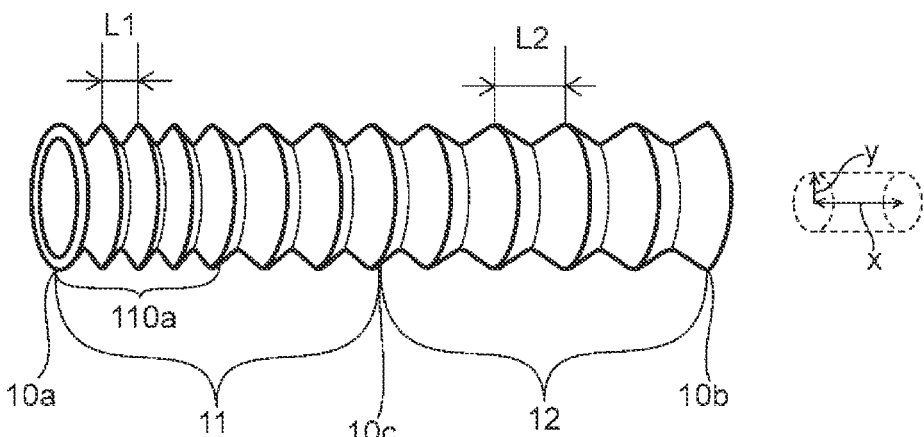

BLOOD VESSEL COVER

TECHNICAL FIELD

The present invention relates to a blood vessel cover used for an anastomosis site where blood vessels are anastomosed, and for example, a blood vessel cover that can be placed on an outer circumference of a vein at an anastomosis site where an artery or an artificial blood vessel that is anastomosed to an artery is anastomosed to the vein to form a shunt construction.

BACKGROUND ART

For patients with serious kidney diseases including renal failure, hemodialysis treatment is regularly performed, in which blood is taken from the patient's body, waste products, excess water and minerals are removed with a dialyzer, and then the blood is returned to the patient's body. When hemodialysis is performed, a special needle is usually inserted into a vein. At this time, since the blood flow in the vein is not sufficient to carry out dialysis, the vein is anastomosed to an artery. Such a vessel is called a shunt, and the shunt is usually formed by making an incision in the skin of the arm to expose the artery and vein, making a small incision in the artery to which the vein is anastomosed, and diverting some of the blood flow from the artery to the vein. The vein may be directly anastomosed to the artery, or an artificial blood vessel may be placed between the artery and the vein by anastomosing one end of the artificial blood vessel to the small incision of the artery and anastomosing the other end of the artificial blood vessel to the vein.

At a shunt construction, since there is a significant difference in elasticity between the artery and vein, when beating blood flows with high blood pressure in the artery flow into the vein that has markedly high extensibility at low pressure and has low elasticity at high pressure, blood turbulence and stress changes to the vein wall occur. This unusual blood flow condition results in intimal thickening of the anastomosis site and outflow tract vein, which can easily lead to pathological changes such as stenosis, occlusion, and thrombus formation. Failure to regulate shunt blood flow conditions at a high burden to the organism can lead to more extensive local pathologies (e.g., varicose formation or stenosis of downstream veins, Steel's syndrome due to excessive shunt blood flow) or systemic pathologies (e.g., heart failure due to markedly increased venous annular flow).

If this unusual blood flow condition is within the range that the body can tolerate, the body's protective and adaptive response may include appropriate remodeling due to changes in vein wall elasticity, etc., and the patient may escape stenosis or obstruction due to intimal thickening, or the shunt blood flow condition may be self-regulated to a state that is not burdensome to the body. However, if this unusual blood flow condition exceeds the local or systemic conditions of the shunt (diabetes, hypertension, arteriosclerosis, blood status, etc.), the appropriate protective or adaptive response does not occur and becomes a pathological biological reaction, causing a local or systemic pathologies.

To address these issues, vascular banding is used, for example, in Non-patent document 1, where the vein wall is reinforced from the outside to prevent excessive blood pressure and consequent hyperextension and blood turbulence in the inner veins, in order to control the rapid increase in blood flow immediately after and during the early phase of the procedure. Patent document 1 discloses a covering for reinforcing natural veins for use as surgical implants, which is a mesh fabric net covering made by forming a knitted fabric that is seamless, tubular, and substantially pile-less. Patent documents 2 and 3 disclose that arteriovenous grafts (AVG) wrapped by a constrictive fiber matrix of biodegradable polymers show a throbbing radial deviation similar to the carotid artery.

RELATED ART DOCUMENTS

Patent Documents

Patent Document 1: JP 2004-535896 T
Patent Document 2: JP 2010-516437 T
Patent Document 3: JP 2013-509258 T

Non-Patent Document

Non-patent document 1: "I Blood Access Problems associated with blood flow failure" by Hiroaki Haruguchi, Nihon Toseki Igakkai Zasshi Vol. 15, No. 1, 68-70, 2000

SUMMARY OF THE INVENTION

Problems to be Solved by the Invention

However, the above-described vascular banding could not sufficiently prevent lesions such as intimal thickening. In the conventional vascular banding, the reinforced vein wall is modified (arterialized) into an arterial wall-like structure only under certain conditions, but the blood pressure and pulsation are not buffered and delivered downstream as blood flows from the reinforced site to the non-reinforced vein, which is not a fundamental solution to the cause of intimal thickening. To solve this, the blood pressure and pulsation should be gradually reduced downstream from the anastomosis site, and the most downstream venous side should be remodeled to a state where only low pressure without pulsatility is applied, i.e., a low-pressure buffer system vessel.

The present invention was made in view of the above circumstances, and the objective thereof is to provide a blood vessel cover that can reduce or prevent intimal thickening by remodeling the vein into a buffer system vessel that can deliver blood to downstream vein while gradually reducing blood pressure, pulse pressure, and blood flow through the lumen.

Means for Solving the Problems

A blood vessel cover in accordance with an embodiment of the present invention that can solve the above problems is as follows.

[1] A cylindrical blood vessel cover that is continuous around the entire circumference and to be placed on an outer circumference of a vein that is anastomosed to an artery or to an artificial blood vessel, comprising a portion (A), wherein the portion (A) has a 20% elastic index of 1.2 N or less when an inner diameter of the blood vessel cover is expanded in a radial direction by 20% from its natural state, and the 20% elastic index is measured by preparing a cylindrical sample that has a length of 5 mm in an axial direction and is continuous around the entire circumference over the entire axial direction by cutting the blood vessel cover perpendicular to the axial direction along a circumferential cut line of the blood vessel cover;

inserting a first pin and a second pin each having a diameter d of 0.75 mm into a lumen of the cylindrical sample so that each of the first pin and the second pin is parallel to the axial direction of the cylindrical sample;

fixing the first pin;

pulling the second pin towards outside of a radial direction of the cylindrical sample;

measuring a pulling force $F_{1.2}$ when $\pi d+2L$ becomes 1.2 times a perimeter of the cylindrical sample in its natural state given that a distance between the first pin and the second pin is L; and dividing the pulling force $F_{1.2}$ by a strain $[(1.2-1.0)/1.0]$ to obtain the 20% elastic index.

The blood vessel cover having the above configuration has the portion (A) having the 20% elastic index of as small as 1.2 N or less, which allows the vein to be loosely covered when placed on the outer circumference of the vein of the shunt construction, and allows the vein at the shunt construction to be remodeled so that it becomes a buffer vessel where the pulsatile blood flow with high arterial pressure that flows into the vein at the shunt construction can be gradually buffered by the portion covered by the blood vessel cover and finally shifted to venous blood flow. In addition, while veins may gradually grow outward in the process of remodeling into buffered vessels, the blood vessel cover with the above configuration has the portion (A) having the 20% elastic index of as small as 1.2 N or less does not interfere with this growth, and thus, can maintain a wide lumen of the covered blood vessel to ensure sufficient blood flow. Thus, the blood vessel cover of the present invention enables shunt construction that allows sufficient blood flow while reducing lesions such as intimal thickening by remodeling the vein into a buffer system vessel.

The blood vessel cover in accordance with embodiments of the present invention preferably includes the following [2] to [12].

[2] The blood vessel cover according to [1], wherein the 20% elastic index of the portion (A) is 0.1 mN or more.

The lower limit of the 20% elastic index of the above predetermined value allows the blood vessel to be covered with more than a predetermined force even when the blood pressure applied to the vessel is weak.

[3] The blood vessel cover according to [1] or [2], wherein in the axial direction, the blood vessel cover has a first end and a second end; the blood vessel cover has a first part from the first end to a midpoint between the first end and the second end, and a second part from the midpoint to the second end; and the portion (A) is located in the first part.

The portion (A) with the 20% elastic index of 1.2 N or less is arranged at least in the first part, which allows loose coverage of the upstream side of the vein when the first end of the blood vessel cover is placed upstream of the vein in the shunt construction, thus, bringing about changes that remold the vein into a buffer system vessel from upstream. This allows for easier remodeling of the vein into a buffer system vessel and securing of blood flow.

[4] The blood vessel cover according to [3], wherein the blood vessel cover has a first end part from the first end to a midpoint of the first part in the axial direction, and the portion (A) is located in the first end part.

The portion (A) is arranged especially in the first end part among the first part, which allows loose coverage of the most upstream side of the vein when the first end of the blood vessel cover is placed upstream of the vein in the shunt construction, resulting in easier remodeling of the vein into a buffer system vessel and securing of blood flow.

[5] The blood vessel cover according to any one of [1] to [4], wherein the entire blood vessel cover is the portion (A).

This allows the 20% elastic index to be 1.2 N or less over the entire axial direction of the blood vessel cover, so that the entire range of the vein covered by the blood vessel cover can be loosely covered, facilitating remodeling of the vein into a buffer system vessel, and maintaining a wider lumen for the vein, which leads to secure blood flow.

[6] The blood vessel cover according to any one of [1] to [5], wherein in the axial direction, the blood vessel cover has a first end and a second end; and the blood vessel cover has a first part from the first end to a midpoint between the first end and the second end, and a second part from the midpoint to the second end; and the 20% elastic index in the second part is smaller than the 20% elastic index in the first part.

This allows for looser coverage of the downstream side of the vein when the first part of the blood vessel cover is placed upstream of the vein in the shunt construction, thus gradually bringing about changes that remodel the vein into a buffer system vessel from upstream to downstream. This allows for easier remodeling of veins into buffer system vessels and securing of blood flow.

[7] The blood vessel cover according to any one of [1] to [6], wherein in the axial direction, the blood vessel cover has a first end and a second end; and the blood vessel cover has a first part from the first end to a midpoint between the first end and the second end, a second part from the midpoint to the second end, a first end part from the first end to a midpoint of the first part, a middle part from the midpoint of the first part to a midpoint of the second part, and a second end part from the midpoint of the second part to the second end; and the blood vessel cover satisfies the relationship Ea>Ec>Eb given that the 20% elastic index in the first end part is Ea, the 20% elastic index in the middle part is Ec, and the 20% elastic index in the second end part is Eb.

This allows the vein to be loosely covered from upstream to midstream and further downstream when the first end part of the blood vessel cover is placed on the upstream side of the vein in the shunt construction, thereby gradually bringing about changes that remodel the vein into a buffer system vessel from upstream to midstream and further downstream. This allows for easier remodeling of veins into buffer system vessels and securing of blood flow.

[8] The blood vessel cover according to any one of [1] to [7], a length of the portion (A) in the axial direction is 50% or longer of an outer diameter of the artery or artificial blood vessel to which the vein is anastomosed.

The portion (A) of the blood vessel cover with a 20% elastic index of 1.2 N or less is longer than specified, which allows for easier remodeling of veins covered by the blood vessel cover into buffer system vessels and securing of blood flow.

[9] The blood vessel cover according to according to [1] to [8], wherein an inner diameter of the blood vessel cover is expandable by at least 100% in the radial direction from its natural state throughout the axial direction.

This makes it easier to maintain a wide vessel lumen and ensure adequate blood flow because the gradual outward growth of the blood vessel covered by the blood vessel cover is not interfered during the remodeling process.

[10] The blood vessel cover according to any one of [1] or [9], having a length in the axial direction of 5 mm or longer.

Covering the vein at the shunt construction with the blood vessel cover having a length longer than a predetermined length facilitates remodeling of the vein into a buffer system vessel.

[11] The blood vessel cover according to any one of [1] to [10], comprising at least one of knitted fabric, woven fabric, and nonwoven fabric as a partial or whole component.

[12] The blood vessel cover according to any one of [1] to [11], having a bellows structure with periodically repeating peaks and valleys in the axial direction, wherein in the axial direction, the blood vessel cover has a first end and a second end; the blood vessel cover has a first part from the first end to a midpoint between the first end and the second end, a second part from the midpoint to the second end, and a first end part from the first end to a midpoint of the first part; and in the axial direction, a distance between adjacent peaks in the second part is longer than a distance between adjacent peaks in the first end part.

This facilitates remodeling of the vein into a buffer system vessel, because placing the first end part of the blood vessel cover on the upstream side of the vein at the shunt construction allows the downstream side of the vein to be more loosely covered.

Effects of the Invention

Covering the vein at the shunt construction by the blood vessel cover of the present invention having the above configuration can suppress incompatibility of vessel wall elasticity, turbulent blood flow, and excessive high flow rate to reduce or prevent intimal thickening by gradually changing the wall structure of the vein from the anastomosis site to the downstream to gradually change shear stress, pressure orthogonal to the vascular wall, blood flow, flow velocity, and range of change with beating in the interior of the covered vein. The reason why the blood vessel cover of the present invention achieves these effects may be due to the following.

Both arteries and veins consist of an intima, a tunica media, and an adventitia, and the arteries have the tunica media consisting of smooth muscle cell-rich smooth muscle layer and an elastic fiber layer including collagen fibers. The arteries have thick smooth muscle and elastic fiber layers so that pulsation change in the vessel wall is little to prevent turbulence generation and fluctuations in abrasion stress, even under the pressure of pulsating luminal blood flow. On the other hand, the veins have thin vessel walls and do not have the thick smooth muscle and elastic fiber layers as the arteries do. When arterial blood flows directly into such veins via arteriovenous shunts, lesions such as intimal thickening occur due to the substantial difference in elasticity between arteries and veins as described above. To prevent this, while the most upstream part of the vein at a shunt construction, i.e., the anastomosis site, is subjected to 100% pulsatile arterial pressure, the vein at the shunt construction needs to be remodeled into a buffer system vessel, which gradually decreases the blood pressure, pulsatility, blood flow, and maximum flow velocity towards the downstream of the vein to make the most downstream vein have low non-pulsatile pressure.

The blood vessel cover of the present invention, having the above configuration, can make the vein at the shunt construction remodeled into a buffer system vessel so that the pulsatile blood flow with high arterial pressure entering the veins at arteriovenous or artificial blood vessel-vein shunt construction can be gradually buffered downstream and finally shifted to venous blood flow, which is a buffer system vessel. As a result, blood turbulence and pulsatile changes in the venous wall can be suppressed, preventing lesions such as intimal thickening.

In addition, the blood vessel cover of the present invention, having the above configuration, does not interfere with the gradual outward growth of veins in the process of remodeling them into low-pressure buffer system vessels, and as a result, the lumen of the vessel can be maintained wide enough to ensure sufficient blood flow. This enables shunt construction that ensure sufficient blood flow while suppressing lesions such as intimal thickening.

BRIEF DESCRIPTION OF THE DRAWINGS

FIG. 1 is a schematic view of one example of shunt construction.

FIG. 2 is a schematic view of another example of shunt construction.

FIG. 3 is a perspective view of a blood vessel cover in accordance with one embodiment of the present invention when placed on an outer circumference of a vein at shunt construction.

FIG. 4 is a perspective view of a blood vessel cover in accordance with one embodiment of the present invention.

FIG. 5 is a perspective view of a blood vessel cover in accordance with another embodiment of the present invention.

FIG. 6 is a perspective view of a blood vessel cover in accordance with still another embodiment of the present invention.

FIG. 7 is a perspective view of a blood vessel cover in accordance with still another embodiment of the present invention.

FIG. 8 is a perspective view showing the measurement method of the elastic index.

FIG. 9 is a plan view of FIG. 8 viewed from above.

FIG. 10 is a perspective view of a blood vessel cover in accordance with still another embodiment of the present invention.

MODE FOR CARRYING OUT THE INVENTION

Hereinafter, the present invention will be described based on the following embodiments, however, the present invention is not limited by the following embodiments and can be altered in design within a scope in compliance with the intent described above and below, and all the changes are to be encompassed within a technical scope of the present invention. Note that, in each drawing, hatching, reference signs for components, and the like may be omitted for convenience of description, and in such a case, the specification and other drawings are to be referred to. Furthermore, since the dimensions of the various components in the drawings are provided for the purpose of facilitating the understanding of the feature of the present invention, the dimensions may differ from the actual dimensions in some cases.

A blood vessel cover in accordance with embodiments of the present invention will be described referring to the figures. Note that the present invention is not limited to the embodiments shown in the figures. FIG. 1 is a schematic view in which an autologous vein is anastomosed to a small incision in an artery at a shunt construction, and FIG. 2 is a schematic view in which one end of an artificial blood vessel is anastomosed to a small incision in an artery and the other end of the artificial blood vessel is anastomosed to a vein.

FIG. 3 is a perspective view of a blood vessel cover in accordance with one embodiment of the present invention when placed on an outer circumference of a vein at shunt construction. FIGS. 4 to 7, and 10 are perspective views of a blood vessel cover in accordance with different embodiments of the present invention. FIG. 8 is a perspective view showing the measurement method of the elastic index, and FIG. 9 is a plan view of FIG. 8 viewed from above.

A shunt construction 1 can be formed by performing an arteriovenous anastomosis as shown in FIG. 1 or an artificial blood vessel-vein anastomosis as shown in FIG. 2.

As shown in FIG. 1, the shunt construction 1 can be formed by anastomosing a vein 4 to a small incision in an artery 3 in an arm 2 and allowing blood to flow from the artery 3 to the vein 4. In this case, blood flows from the artery 3 through an anastomosis site 6 to the vein 4 in the direction indicated by an arrow B.

Alternatively, as shown in FIG. 2, the shunt construction 1 can be formed by anastomosing one end of an artificial blood vessel 5 to a small incision in an artery 3 in an arm 2 and the other end of the artificial blood vessel 5 to a vein 4. In this case, blood flows from the artery 3 to the artificial blood vessel 5 and further to the vein 4 through an anastomosis site 6 in the direction indicated by an arrow B.

A blood vessel cover 10 in accordance with embodiments of the present invention can be placed on the periphery of the vein 4 from the anastomosis site 6 to downstream in either the arteriovenous anastomosis shown in FIG. 1 or the artificial blood vessel-vein anastomosis shown in FIG. 2, and can remodel the vein 4 into a buffer system vessel.

In all of the above cases, for example, as shown in FIG. 3, the blood vessel cover 10 is preferably placed from the most upstream side of the vein 4 at the anastomosis site 6. The blood vessel cover 10 has a first end 10a and a second end 10b, the first end 10a is preferably placed on the most upstream side of the vein 4 at the anastomosis site 6, and the second end 10b is preferably placed downstream of the vein 4 away from the anastomosis site 6.

Although not shown in the figures, the blood vessel cover 10 may be arranged to cover not only the vein 4 but also a part of the artery 3 and the artificial blood vessel 5 on the side of the anastomosis site 6 even when anastomosed to either the artery 3 or the artificial blood vessel 5.

The blood vessel cover 10 is formed in a continuous cylindrical shape over its entire circumference and has an axial direction x and a radial direction y. The axial direction x of the blood vessel cover 10 is the direction in which a central axis C of the blood vessel cover 10 extends, and the radial direction y of the blood vessel cover 10 is the direction connecting the central axis C of the blood vessel cover 10 and a point on the outer edge of the blood vessel cover 10 in a cross-section perpendicular to the axial direction x. The blood vessel cover 10 may be a knitted fabric, woven fabric, or net that is continuous around its entire circumference. Although the knitted fabric, woven fabric, and net have knitted stitches or weaves, those knitted stitches and weaves are not discontinuous portions of the blood vessel cover 10, and the knitted fabric, woven fabric, or net can form the above-described "continuous cylindrical shape."

As shown in FIG. 3, the blood vessel cover 10 is preferably flexible, and the axial direction x of the blood vessel cover 10 is preferably able to follow and curve with the direction of extension of the vein 4 to be covered.

As shown in FIG. 4 to FIG. 8, the blood vessel cover 10 preferably has a circular or oval lumen in shape in the cross-section in the radial direction y. Depending on the material constituting the blood vessel cover 10 and the structure of the blood vessel cover 10, the outer edge of the shape in the cross-section in the radial direction y may have fine irregularities.

Alternatively, although not shown in the figures, the blood vessel cover 10 may have a collapsed lumen under its own weight in its natural state. In such a case, the lumen can be widened to define the same axial direction x, radial direction y, and shape in a cross-section in the radial direction y as described above. The method of widening the lumen collapsed by its own weight includes, for example, a method where a tube whose lumen does not collapse under its own weight and which has a central axis parallel to the central axis C of the blood vessel cover 10 and is inscribed on the inner wall of the blood vessel cover 10 is inserted into the lumen of the blood vessel cover 10.

The blood vessel cover 10 is cylindrical, and may have joints, for example, formed by rounding a flat-shaped material into a tubular shape and joining it by sutures or other methods. In such a case, the joints including sutures are preferably formed on the outer surface of the blood vessel cover 10. This prevents the joints from affecting the vein 4. Alternatively, a seamless tubular member without joints may be formed into the blood vessel cover 10 by using a molded or knitted member.

The inner diameter of the blood vessel cover 10 is the diameter of the lumen in the cross-section in the radial direction y, and when the shape of the lumen in the cross-section in the radial direction y is circular, it is the diameter of the circle. The inner diameter of the blood vessel cover 10 can also be defined as the value obtained by dividing the circumference of the inner wall of the blood vessel cover 10 in the cross-section in the radial direction y by the circumference ratio π. According to this, the inner diameter of the blood vessel cover 10 can be obtained even when the cross-sectional shape of the blood vessel cover 10 in the radial direction y is not circular or when the lumen of the blood vessel cover 10 is collapsed by its own weight.

The blood vessel cover 10 has a portion (A) having a 20% elastic index of 1.2 N or less when the inner diameter of the blood vessel cover 10 is expanded in the radial direction y by 20% from its natural state. The 20% elastic index is measured by preparing a cylindrical sample 100 that has a length of 5 mm in the axial direction x and is continuous around the entire circumference over the entire axial direction x without a break in the wall by cutting the blood vessel cover 10 perpendicular to the axial direction x along a circumferential cut line of the blood vessel cover 10, inserting a first pin 101 and a second pin 102 each having a diameter d of 0.75 mm into a lumen of the cylindrical sample 100 so that each of the first pin 101 and the second pin 102 is parallel to the axial direction of the cylindrical sample 100, fixing the first pin 101, pulling the second pin 102 towards outside of the radial direction of the cylindrical sample 100, measuring a pulling force $F_{1.2}$ when πd+2L becomes 1.2 times a perimeter of the cylindrical sample 100 in its natural state given that a distance between the first pin 101 and the second pin 102 is L, and dividing the pulling force $F_{1.2}$ by a strain [(1.2−1.0)/1.0] to obtain the 20% elastic index.

Here, the cylindrical sample 100 that has a length of 5 mm in the axial direction x and is continuous around the entire circumference over the entire axial direction x may be a knitted fabric, woven fabric, or net that is continuous around the entire circumference. Gaps formed by knitted stitches and weaves of the knitted fabric, woven fabric, or net are not included in the "break" in the above "sample without a break."

Because the blood vessel cover 10 has the portion (A) having the 20% elastic index of as small as 1.2 N or less, the vein 4 can be loosely covered when the blood vessel cover 10 is placed on the outer periphery of the vein 4 at the shunt construction 1, so that the vein 4 at the shunt construction 1 can be remodeled to become a buffer system vessel where the pulsatile blood flow with high arterial pressure that flows into the vein 4 at the shunt construction 1 is gradually buffered and can finally be transferred to venous blood flow at the part covered by the blood vessel cover 10. As a result, blood flow turbulence and pulsatile changes in the vein wall are suppressed, and lesions such as intimal thickening can be prevented.

More specifically, by gradually forming a two-layer structure, in the wall of the vein 4 at the shunt construction 1, comprising a smooth muscle layer containing elastic fiber layer thicker than the smooth muscle layer of normal veins and an elastic fiber layer containing collagen fibers thicker than the smooth muscle layer on the outside of the smooth muscle layer, the vein 4 at the shunt construction 1 can be remodeled into a low-pressure buffer system vessel.

The difference between the above-described buffer system vessel and normal arteries is explained below. Blood vessels are composed of three layers: intima, tunica media, and adventitia. Of these, the intima contributes significantly to the anti-coagulability, but its mechanical contribution is very small. The composition of the mechanical elements of the arteries of the extremities, which are normally used for dialysis, consists largely of the tunica media containing some elastic fibers and abundant smooth muscle and the adventitia consisting of elastic fibers and collagen fibers etc. outside the tunica media. In other words, these arteries have very abundant smooth muscle and relatively fewer elastic fibers (the composition of "smooth muscle>elastic fibers"). The elastic fibers, due to their elasticity, have a buffering function like a lubber tube, resisting and relaxing the high pulsatile arterial blood pressure. On the other hand, the smooth muscle, which is muscle, has a more active mechanical function, resisting arterial blood pressure, and at the same time, has the active and proactive function of delivering high pulsatile arterial blood pressure to the periphery without attenuation. Because of this pressure delivering function of the abundant smooth muscle of arteries, the blood pressure is almost the same whether it is a large artery with an inner diameter of centimeters or a small artery with an inner diameter of a fraction of millimeter. In other words, normal arteries (with the configuration of "smooth muscle>elastic fibers") do not have the ability to buffer high pulsatile arterial pressure due to the function of the abundant smooth muscle. On the other hand, when a vein at the shunt construction is remodeled into a buffer system vessel, the ratio of elastic fibers and smooth muscle is opposite of that in normal arteries, with elastic fibers abundant and smooth muscle relatively thin (configuration of "elastic fibers>smooth muscle"). Accordingly, in buffer system vessels, the pressure buffering function is dominant over the pressure delivery function. In buffer system vessels, while maintaining the above configuration "elastic fibers>smooth muscle", i.e., the buffering function, the whole system gradually becomes thin and transformed to veins, i.e., gradually transformed to the normal veins as the buffered pressure decreases. If, hypothetically, the vein wall changes to normal artery-like, this is arterialization (remodeling into an artery) and not remodeling into the buffer system vessel. If that arterialization gradually weakens and spontaneously transitions to completely normal veins at the downstream part, it means that the vessel maintaining the configuration of "smooth muscle>elastic fibers" gradually becomes thin and transformed to veins, causing pathological changes in the downstream veins since it has no buffering function and high pulsatile blood pressure acts on the venous wall. This is the clear functional difference between the gradual thinning of the buffer system vessels and their transition to normal veins and the gradual thinning of normal arterial-like vessels and their transition to normal veins.

The blood vessel cover 10 in accordance with embodiments of the present invention, having the above configuration, can loosely cover the vein 4 at the shunt construction 1, allowing the wall structure of the vein 4 to be changed as described above and remodeled into a buffer system vessel.

Furthermore, while the vein 4 may gradually grow outward in the process of remodeling into a buffer system vessel, the blood vessel cover 10 in accordance with embodiments of the present invention has the portion (A) having the 20% elastic index of as small as 1.2 N or less, thus reducing the inhibition by the blood vessel cover 10 to the growth of the vein 4 and allowing the lumen of the vein 4 to be kept wide to ensure sufficient blood flow.

This makes it possible to form the shunt construction 1 that can ensure sufficient blood flow while suppressing lesions such as intimal thickening, according to the blood vessel cover 10 in accordance with embodiments of the present invention.

The 20% elastic index in the portion (A) is preferably 1.1 N or less, more preferably 1 N or less, even more preferably 0.9 N or less, and may be 0.8 N or less, 0.6 N or less, and 0.4 N or less. The above effect can be achieved by the portion (A) having the 20% elastic index in the above range. The 20% elastic index in the portion (A) is preferably 0.1 mN or more, more preferably 0.5 mN or more, and even more preferably 1 mN or more. The 20% elastic index in the portion (A) above a predetermined value allows the blood vessel to by covered with more than a predetermined force even when the blood pressure applied to the vessel is weak.

The method of measuring the 20% elastic index is described with reference to FIG. 8 and FIG. 9. The cylindrical sample 100 is prepared by cutting the blood vessel cover 10 perpendicular to the axial direction x along a circumferential cut line of the blood vessel cover 10. The blood vessel cover 10 is cut along the cut plane perpendicular to the axial direction x, i.e., the circumferential cut line, all the way around, so that the cylindrical sample 100 having a length of 5 mm in the axial direction x and continuous around the entire circumference over the entire axial direction x without a break in the wall. Next, as shown in FIG. 8, the first pin 101 and the second pin 102 each having a diameter d of 0.75 mm are inserted into the lumen of the cylindrical sample 100 so that each of the first pin 101 and the second pin 102 is parallel to the axial direction of the cylindrical sample 100. The length of the first pin 101 and the second pin 102 is not limited, but preferably longer than the length of the cylindrical sample 100 in the axial direction x. The first pin 101 is fixed, the second pin 102 is pulled towards outside of the radial direction of the cylindrical sample 100, a pulling force $F_{1.2}$ when $\pi d + 2L$ becomes 1.2 times a perimeter of the cylindrical sample 100 in its natural state given that a distance between the first pin 101 and the second pin 102 is L is measured, and the pulling force $F_{1.2}$ is divided by the strain $[(1.2-1.0)/1.0]$ to obtain the 20% elastic index.

The distance L between the first pin 101 and the second pin 102 is, as shown in FIG. 9, a distance between the center of the first pin 101 and the center of the second pin 102. The inner diameter of the cylindrical sample 100 is equal to the sum of ½ of the circumference ad of the first pin 101, ½ of the circumference ad of the second pin 102, and twice the distance L between the first pin 101 and the second pin 102, i.e., πd+2L. Accordingly, the 20% elastic index can be obtained by dividing the pulling force $F_{1,2}$ when the inner diameter of the cylindrical sample 100 is expanded by 20% from its natural state, i.e., when πd+2L becomes 1.2 times the perimeter of the cylindrical sample 100 in its natural state by the strain [(1.2−1.0)/1.0].

The portion (A) having the 20% elastic index of 1.2 N or less may be provided continuously or spaced apart in the axial direction x. The portions of the blood vessel cover 10 other than the portion (A) may have a 20% elastic index of greater than 1.2 N, but portions other than the portion (A) are preferably 75% or shorter of the total length of the blood vessel cover 10 in the axial direction x of the blood vessel cover 10, more preferably 50% or shorter, even more preferably 30% or shorter, particularly preferably 10% or shorter, and most preferably 0%.

The inner diameter of the blood vessel cover 10 can be appropriately determined depending on the vessel diameter to be applied, and for example, preferably 1 mm or more, more preferably 2 mm or more, even more preferably 3 mm or more, and may be 4 mm or more. The inner diameter of the blood vessel cover 10 is, for example, preferably 10 mm or less, more preferably 9 mm or less, and even more preferably 8 mm or less. The blood vessel cover 10 may have different inner diameter depending on the position in the axial direction x. The blood vessel cover 10 may have a straight shape with a similar inner diameter from the first end 10a to the second end 10b, or may have a tapered shape with a gradual increase in inner diameter from the first end 10a to the second end 10b. The blood vessel cover 10 may also have a bellows shape with a periodically changing inner diameter in the axial direction x.

As shown in FIG. 4 and FIG. 5, the blood vessel cover 10 has a first part 11 from the first end 10a to a midpoint 10c between the first end 10a and the second end 10b and has a second part 12 from the midpoint 10c to the second end 10b in the axial direction x, and the portion (A) is preferably located in the first part 11. When the portion (A) having the 20% elastic index of as small as 1.2 N or less is located in the first part 11, the first part 11 placed on the upstream side of the vein 4 at the shunt construction 1 can loosely cover the upstream side of the vein 4, bringing about changes upstream that remodel the vein 4 into a buffer system vessel. This allows for easier remodeling of the vein 4 into a buffer system vessel and ensuring the amount of blood flow. The portion (A) may be located only in the first part 11, or may be located also in the second part 12.

In this case, as shown in FIG. 6 and FIG. 7, the blood vessel cover 10 has a first end part 100a from the first end 10a to a midpoint of the first part 11 in the axial direction x, and the portion (A) is preferably located in the first end part 100a. When the portion (A) having the 20% elastic index of as small as 1.2 N or less is located in the first end part 100a, the first end part 100a placed on the upstream side of the vein 4 at the shunt construction 1 can loosely cover the upstream side of the vein 4, allowing for more effective remodeling of the vein 4 into a buffer system vessel and securing of the lumen diameter of the vein 4.

FIG. 4 to FIG. 7 show schematically the locations where the portion (A) is arranged, but the sections where the blood vessel cover 10 has the portion (A) are not limited to these figures, and any section may have the portion (A) as long as it meets each of the above requirements.

Preferably, the entire blood vessel cover 10 is the portion (A). This allows the entire blood vessel cover 10 to have the 20% elastic index of 1.2 N or less, enabling the entire area of the vein 4 covered by the blood vessel cover 10 to be loosely covered, further facilitating remodeling of the vein 4 into a buffer system vessel and making it easier to maintain the lumen of the vein 4 wide to secure blood flow.

The blood vessel cover 10 has the first part 11 from the first end 10a to the midpoint 10c between the first end 10a and the second end 10b and the second part 12 from the midpoint 10c to the second end 10b, and the 20% elastic index in the second part 12 is preferably smaller than the 20% elastic index in the first part 11. This allows the downstream side of the vein 4 to be more loosely covered when the first part 11 of the blood vessel cover 10 is placed on the upstream side of the vein 4 at the shunt construction 1, allowing the vein 4 to be gradually remodeled from upstream to downstream, buffering the transmural pressure, shear stress, pulsating pressure of the beat, flow velocity of blood, and the amount of blood flow, resulting in the change from the upstream to downstream part. This allows for easier remodeling of the vein into a buffer system vessel and securing the amount of blood flow.

The 20% elastic index of the part having a length of 5 mm from the midpoint 10c towards the side of the second end 10b in the axial direction x is preferably 0.1 times or more and 0.98 times or less, 0.96 times or less, 0.9 times or less, 0.8 times or less, or 0.7 times or less the 20% elastic index of the part having a length of 5 mm from the first end 10a towards the side of the second end 10b in the axial direction x. The 20% elastic index of the part having a length of 5 mm from the midpoint 10c towards the side of the second end 10b in the axial direction x may be 0.2 times or more or 0.3 times or more the 20% elastic index of the part having a length of 5 mm from the first end 10a towards the side of the second end 10b in the axial direction x. Comparing to the 20% elastic index of the part having a length of 5 mm in the axial direction x from the first end 10a to towards the side of the second end 10b. i.e., the part of the blood vessel cover 10 that covers the most upstream part when the first end 10a is placed on the upstream side of the vein 4 at the shunt construction 1, the part having a length of 5 mm in the axial direction x from the midpoint 10c towards the side of the second end 10b, i.e., the part of the blood vessel cover 10 that covers the downstream side when the first end 10a is placed on the upstream side of the vein 4 at the shunt construction 1 has the 20% elastic index in the above range, allowing the vein 4 to be gradually remodeled from the upstream side into a buffer system vessel.

The blood vessel cover 10 has, in the axial direction x, the first part 11 from the first end 10a to the midpoint 10c between the first end 10a and the second end 10b, the second part 12 from the midpoint 10c to the second end 10b, a first end part 100a from the first end 10a to a midpoint of the first part 11, a middle part 100c from the midpoint of the first part 11 to a midpoint of the second part 12, and a second end part 100b from the midpoint of the second part 12 to the second end 10b, and the blood vessel cover 10 satisfies the relationship Ea>Ec>Eb given that the 20% elastic index in the first end part 100a is Ea, the 20% elastic index in the middle part 100c is Ec. and the 20% elastic index in the second end part 100b is Eb. This allows for loose coverage of the vein 4 from upstream to midstream and further downstream when the first end part 100a of the blood vessel cover 10 is placed on the upstream side of the vein 4 at the shunt construction 1, allowing a gradual change in the remodeling of the vein 4 into a buffer system vessel from upstream to midstream and further downstream. This makes the remodeling of the vein 4 into a buffer system vessel and securing the amount of blood flow easier.

The 20% elastic index Ec in the middle part 100c is preferably 0.05 times or more the 20% elastic index Ea in the first end part 100a, and preferably 0.8 times or less, and may be 0.6 times or less, 0.5 times or less, 0.4 times or less, or 0.3 times or less. The 20% elastic index Eb in the second end part 100b is preferably 0.1 times or more the 20% elastic index Ec in the middle part 100c, and preferably 0.9 times or less, and may be 0.8 times or less, 0.7 times or less, 0.6 times or less, or 0.5 times or less. In all cases, each of Ea, Ec, and Eb is preferably 1 mN or more. When Ea, Ec, and Eb are in the above range, the vein 4 can be gradually remodeled from the upstream side into a buffer system vessel.

The length of the portion (A) in the axial direction x is preferably 50% or longer of the outer diameter of the artery 3 or artificial blood vessel 5 to which the vein 4 is anastomosed. The length of the portion (A) in the axial direction x is more preferably 60% or longer of the anastomosed artery 3 or artificial blood vessel 5, even more preferably 80% or longer, and may be 100% or longer. The upper limit of the length of the portion (A) in the axial direction x is not particularly limited, and may be 2000% or shorter of the anastomosed artery 3 or artificial blood vessel 5, or 1750% or shorter or 1500% or shorter. The portion (A) of the blood vessel cover 10 with the 20% elastic index of 1.2 N or less is longer than a predetermined length, making it easier to remodel the vein 4 covered by the blood vessel cover 10 into a buffer system vessel and to ensure blood flow.

The inner diameter of the blood vessel cover 10 is preferably expandable by at least 50% in the radial direction y from its natural state throughout the axial direction x. This makes it easier to maintain a wide lumen of the blood vessel and ensure adequate blood flow because the blood vessel cover 10 does not interfere with the gradual outward growth of the vessel during the remodeling process.

A 50% elastic index of the portion (A) is preferably 3.2 N or less when the inner diameter is expanded in the radial direction y by 50% from its natural state. The 50% elastic index is measured by preparing a cylindrical sample 100 that has a length of 5 mm in the axial direction x and is continuous around the entire circumference over the entire axial direction x without a break in the wall by cutting the blood vessel cover 10 perpendicular to the axial direction x along a circumferential cut line of the blood vessel cover 10, inserting a first pin 101 and a second pin 102 each having a diameter d of 0.75 mm into a lumen of the cylindrical sample 100 so that each of the first pin 101 and the second pin 102 is parallel to the axial direction of the cylindrical sample 100, fixing the first pin 101, pulling the second pin 102 towards outside of the radial direction of the cylindrical sample 100, measuring a pulling force $F_{1.5}$ when $\pi d+2L$ becomes 1.5 times a perimeter of the cylindrical sample 100 in its natural state given that a distance between the first pin 101 and the second pin 102 is L, and dividing the pulling force $F_{1.5}$ by a strain $[(1.5-1.0)/1.0]$ to obtain the 50% elastic index.

The 50% elastic index of the portion (A) is preferably 3.2 N or less, more preferably 2.5 N or less, even more preferably 2 N or less, and may be 1.8 N or less, 1.5 N or less, 1.2 N or less, 1.1 N or less or 1 N or less. With the portion (A) having the 50% elastic index in the above range, the blood vessel cover 10 can cover the vein 4 with less than a predetermined force even when the blood vessel cover 10 is expanded by 50%, thus achieving the above effect. The 50% elastic index of the portion (A) is preferably 0.1 mN or more, more preferably 0.5 mN or more, and even more preferably 1 mN or more. The 50% elastic index of the portion (A) being the same as or more than a predetermined value allows the blood vessel to be covered with more than a specified force even when the blood pressure applied to the blood vessel is weak.

The significance of the 20% elastic index and 50% elastic index is explained here. In the shunt construction 1, a condition of blood flow that does not normally occur is artificially created, i.e., a condition where high-pressure pulsating arterial blood flow acts directly on the vein wall at high velocity. If the body can tolerate this unusual condition, remodeling into a buffer system vessel occurs as a protective and adaptive responses of the living body. However, as mentioned earlier, the unusual condition exceeding the range in which appropriate protective and adaptive responses occur leads to pathological biological reactions. A 10% to 20% dilatation of the venous inner diameter from its natural state is a relatively small degree of dilatation, and controlling venous dilatation to 20% by the blood vessel cover 10 means that there is sufficient margin to keep it within the appropriate range of protective and adaptive responses, and the occurrence of pathological reaction is almost 100% preventable.

However, when evaluated from the viewpoint of the buffering function of arterial blood flow, it is necessary to consider that if the dilatation is kept within 20% by the blood vessel cover 10, it may not necessarily have a sufficient buffering function, depending on the flow path length and other conditions, and there is a possibility that arterial blood flow may flow into the downstream side with inadequate buffering. In other words, the 20% elastic index of the blood vessel cover 10 can be considered an indicator of the necessary condition for good remodeling, since the absence of pathological reactions is essential for good remodeling, but the 50% elastic index may be also be considered together as an indicator of positive buffering effect.

Considering the case of a continuous 50% dilatation of the vein diameter from its natural state, this is clearly not a normal condition, and the living body will produce a protective and adaptive responses. i.e., remodeling into a buffer system vessel to buffer and alleviate this unusual blood flow condition. Furthermore, when venous inner diameter is dilated by 50%, a clear physical buffering effect is expected. In other words, the 50% elastic index can be an index that comprehensively evaluates both the physical buffering effect and the buffering vascular induction effect of the shunt cover in the vein dilatation state where the protective and adaptive responses that remodel the shunt venous part into a buffer system vessel are actively induced. From the above perspective, two indices, the 20% elastic index and the 50% elastic index, can be used to evaluate the performance of the blood vessel cover.

The method for measuring the 50% elastic index is the same as the method for measuring the 20% elastic index described above, except that the force $F_{1.5}$ is measured when $\pi d+2L$ becomes 1.5 times a perimeter of the cylindrical sample 100 in its natural state.

The inner diameter of the blood vessel cover 10 is preferably expandable by at least 100% in the radial direction y from its natural state throughout the axial direction x. This makes it easier to maintain a wide vessel lumen and ensure adequate blood flow because the gradual outward growth of the vessel covered by the blood vessel cover 10 is not disturbed in the process of remodeling.

The length of the blood vessel cover 10 in the axial direction x is preferably 5 mm or longer. The length of the blood vessel cover 10 in the axial direction x is more preferably 10 mm or longer, even more preferably 20 mm or longer, particularly preferably 30 mm or longer, and may be 40 mm or longer. The length of the blood vessel cover 10 in the axial direction x is preferably 120 mm or shorter, more preferably 100 mm or shorter, and even more preferably 90 mm or shorter. With the length of the blood vessel cover 10 in the axial direction x in the above range, the vein 4 at the shunt construction 1 can be covered with the blood vessel cover 10 longer than specified, facilitating remodeling of the vein 4 into a buffer system vessel.

The blood vessel cover 10 preferably has at least one of knitted fabric, woven fabric, and nonwoven fabric as a partial or whole component. With these materials, it is easy to form an elastic deformable blood vessel cover 10.

The type of knitted fabric is not limited and may be warp or weft knitting. Examples of knitting texture of the warp knitting include half knitting, back half knitting, quinz coat knitting, and satin knitting. The weft knitting includes circular knitting and flat knitting, and examples of knitting texture of the weft knitting include plain knitting, rib knitting, double side knitting, milan-rib knitting, and jacquard knitting. In view of excellence in elasticity, the knitted fabric is preferably composed of a weft knitted fabric. The type of woven fabric is not limited and may be plain weave, twill weave, vermillion weave, etc. Alternatively, the blood vessel cover 10 may composed of nonwoven fabric made by any method, such as melt-blown, needle-punched, spun-laced, electrospun, etc.

The blood cover 10 may be made of a combination of two or more different materials, for example, part of the cover is made of knitted fabric and the rest of the cover is made of another material, for example, nonwoven fabric.

The property of the wall of the shunt cover in which plastic deformation is predominant has a better buffering function than that in which elastic deformation is predominant. Therefore, the yarns forming knitted, woven, and nonwoven fabrics are also preferably composed of resin materials in which plastic deformation is predominant. For example, the yarns in which plastic deformation is predominant are exemplified by the ones made polyolefin-based resins such as polyethylene and polypropylene; polyamide-based resins such as nylon; polyester-based resins such as polyethylene terephthalate; polyimide-based resins; fluorine-based resins such as PTFE, PFA, and ETFE; and polyvinyl chloride-based resins. The yarns forming the knitted or woven fabric may be composed of resin materials used in artificial blood vessels (e.g., polyester, PTFE), and specifically exemplified by ePTFE, which is stretched PTFE, Dacron (registered trademark), which is polyester fibers made by Dupont. The blood vessel cover 10 may also be composed of biodegradable materials, such as aliphatic polyesters such as polylactic acid, polyglycolic acid, and polyhydroxyalkanoic acid; and aliphatic polyethers. In addition, the yarns forming the knitted or woven fabric may be composed of natural fibers, such as silk and cotton, or combination of resin materials, biodegradable materials, and natural fibers.

As shown in FIG. 10, preferably, the blood vessel cover 10 has a bellows structure with periodically repeating peaks and valleys in the axial direction x, wherein, in the axial direction x, the blood vessel cover 10 has the first end part 100a from the first end 10a to the midpoint of the first part 11, the distance L2 between adjacent peaks in the second part 12 is longer than the distance L1 between adjacent peaks in the first end part 100a. The relatively shorter distance between the peaks of the bellows structure in the first end part 100a and the relatively longer distance in the second part 12 make it easier to cover the downstream side of the vein 4 more loosely when the first end part 100a is placed on the upstream side of the vein 4 at the shunt construction 1, making it easier to remodel the vein 4 into a buffer system vessel and to secure the lumen diameter of the vein 4.

Assessment of whether the vein 4 has been remodeled into a low-pressure buffer system vessel should be confirmed by both morphological confirmation and confirmation by measurement of the buffering effect, as described below. The morphological method can be performed by checking whether a two-layered structure is formed, consisting of a smooth muscle layer containing elastic fibers and an outer layer of elastic fibers containing collagen fibers that are thicker than the smooth muscle layer. Specifically, the vein 4 at the shunt construction 1 is cut out, special stains such as hematoxylin-eosin (HE) stain and Elastica van Gieson (EvG) stain are applied to observe the vein wall cross section under a microscope. For example, with EvG staining, the smooth muscle is stained turbid yellow, the elastic fibers are stained dark purple, and the collagen fibers are stained dark led, so that the evaluation can be done by observing the smooth muscle layer containing elastic fibers and the elastic fiber layer containing collagen fibers to confirm "thickness of the smooth muscle layer containing elastic fibers<thickness of the elastic fiber layer containing collagen fibers."

The method of confirming whether the vein 4 has been remodeled into a buffer system vessel by measuring the buffering effect can be performed by Doppler blood flow measurement and blood flow measurement with a color Doppler ultrasound imaging system.

The present application claims priority based on Japanese Patent Application No. 2021-146520 filed on Sep. 8, 2021. All the contents described in Japanese Patent Application No. 2021-146520 filed on Sep. 8, 2021 are incorporated herein by reference.

EXAMPLES

Hereinafter, the present invention is described with reference to examples. The present invention is not limited by the following examples, can be absolutely carried out with appropriate changes to the examples within a scope in compliance with the intent described above and later, and all the changes are to be encompassed within a technical scope of the present invention.

Measurements and evaluation in the examples are as follows.

(1) 20% Elastic Index

A cylindrical sample that had a length of 5 mm in the axial direction and was continuous around the entire circumference over the entire axial direction without a break in the wall was prepared by cutting the blood vessel cover along the circumferential cut line perpendicular to the axial direction of the blood vessel cover. A first pin and second pin each having a diameter of 0.75 mm were inserted into the lumen of the above cylindrical sample parallel to the axial direction of the cylindrical sample. The first pin was fixed, the second pin was pulled towards outside of the radial direction of the cylindrical sample, and a force at which the sum of twice the distance between the first pin and second pin and ($\pi \times 0.75$ mm) became 1.2 times the perimeter of the cylindrical sample in its natural state was divided by the strain [(1.2–1.0)/1.0] to obtain the 20% elastic index.

(2) 50% Elastic Index

A cylindrical sample that had a length of 5 mm in the axial direction and was continuous around the entire circumference over the entire axial direction without a break in the wall was prepared by cutting the blood vessel cover along the circumferential cut line perpendicular to the axial direction of the blood vessel cover. A first pin and second pin each having a diameter of 0.75 mm were inserted into the lumen of the above cylindrical sample parallel to the axial direction of the cylindrical sample. The first pin was fixed, the second pin was pulled towards outside of the radial direction of the cylindrical sample, and a force at which the sum of twice the distance between the first pin and the second pin and ($\pi \times 0.75$ mm) became 1.5 times the perimeter of the cylindrical sample in its natural state was divided by the strain [(1.5–1.0)/1.0] to obtain the 50% elastic index.

(3) Animal Experiments of Covering Shunt Construction

Beagle dogs (male and female, weighing 9-14 kg) were used. A shunt was created between the carotid artery and the jugular vein, and the blood vessel cover with the shape, material, inner diameter, axial length, and elastic index shown in Table 1 was placed over the vein at the shunt construction for follow-up observation.

(4) Observation of Smooth Muscle Layer and Elastic Fiber Layer Containing Collagen Fibers After the follow-up observation described in the above (3), the beagle dogs were euthanized and the vein at the shunt construction was removed. The removed vein was stained with Elastica van Gieson (EvG) stain, and the cross sections contained in a section having a length of 5 mm in the direction of blood flow from just below the anastomosis site, a section having a length of 5 mm in the direction of blood flow near the midpoint of the vein cover, and a section having a length of 5 mm from the second end of the vein cover were observed under optical microscope.

(5) Measurement of Thickness of Smooth Muscle Layer and Elastic Fiber Layer Containing Collagen Fibers From the micrographs obtained in the above (4), the thickness of each layer of the vein at each distance from the anastomosis site.

(6) Evaluation of Remodeling into Buffer System Vessel

After the follow-up observation in the above (3), the blood flow condition was measured by Doppler blood flow measurement and further diagnosed by color Doppler ultrasound imaging diagnostic unit. In addition to this measurement and diagnosis, the results of the above (4) and (5) were combined to evaluate whether the vein at the shunt construction was remodeled into a buffer system vessel according to the following criteria.

<Evaluation Criteria>

When all of the following criteria (a) to (e) were met, the vein at the shunt construction was evaluated as remodeled into a buffer system vessel ("good" in Table 1), and otherwise, the vein was evaluated as not remodeled ("bad" in Table 1).

(a) The gross findings at autopsy were that the vessel lumen was open and smooth without varicosity or unnatural irregularities in the vessel wall, and that there was no intimal thickening, stenosis, or thrombus formation as pathological findings that affected blood flow.

(b) In the observation in the above (4), a two-layered structure with an inner smooth muscle layer containing elastic fibers that was clearly thicker than the smooth muscle layer and an outer elastic fiber layer containing collagen fibers that was thicker than the smooth muscle layer was observed, and there was no intimal thickening or thrombus formation.

(c) In the measurement in the above (5), the outer elastic fiber layer containing collagen fibers was thicker than the inner smooth muscle layer.

(d) In the Doppler blood flow measurement above, the blood flowed antegradely and the arterial pulsatile blood flow was buffered (pulsatility was gradually lost from upstream to downstream).

(e) In the above diagnosis using the color Doppler ultrasound imaging diagnostic unit, the vessel lumen was open, the vessel wall was smooth, and there was no pathological intimal thickening or thrombus formation that affected blood flow.

Production Example 1

A seamless cylinder was produced using braiding techniques. The yarn used was wooly nylon with 48 threads per circumference. A part having an axial length of 17 mm was shortened to 5 mm to form a bellows shape, and the 20% elastic index and 50% elastic index were measured. The results are shown in Table 1.

Production Example 2

A seamless cylinder was produced using braiding techniques. The yarn used was wooly nylon with 32 threads per circumference. A part having an axial length of 25 mm was shortened to 5 mm to form a bellows shape, and the 20% elastic index and 50% elastic index were measured. The results are shown in Table 1.

Production Example 3

Knitted fabric was formed using processed yarn (multifilament) made of wooly polyester to produce a seamless blood vessel cover having an axial length of 60 mm and a tapered shape. The inner diameter of one end of the blood vessel cover was 3 mm, and the inner diameter of the other end was 10 mm. Cylindrical samples were cut from one end portion and a portion with an inner diameter of 9 mm near the other end of the produced blood vessel cover, respectively, and the 20% elastic index and 50% elastic index were measured for each cylindrical sample. The results are shown in Table 1.

Production Example 4

A seamless blood vessel cover having an axial length of 60 mm and a straight shape the inner diameter of which was 6 mm was produced by cutting out the softest reinforcing portion of the end of a commercially available artificial blood vessel (Thoratec Artificial Blood Vessel, distributed by Goodman Corporation) made of polyurethane foam with an inner diameter of 6 mm. A cylindrical sample was cut from the center of the produced blood vessel cover, and the 20% elastic index and 50% elastic index were measured. The results are shown in Table 1.

TABLE 1

| | Material | Structure | Shape | Inner diameter (mm) | Axial lengtrh (mm) | Elastic index measurement site | 20% elastic index (N) | 50% elastic index (N) |
|---|---|---|---|---|---|---|---|---|
| Production example 1 | wooly nylon | knitted | bellows | 6 | 35 | central part | 1.05 | 3.02 |
| Production example 2 | wooly nylon | knitted | bellows | 6 | 55 | central part | 0.73 | 1.07 |
| Production example 3 | wooly polyester | knitted | tapered | 3->10 | 60 | first end part second end part | 0.71 0.65 | 1.12 0.94 |
| Production example 4 | polyurehtane | foam | straight | 6 | 55 | central part | 1.48 | 3.4 |

Example 1

A shunt was constructed in the neck of a beagle dog by anastomosing an artery and vein, and the blood vessel cover was placed on the outer circumference of the vein so that the first end of the blood vessel cover obtained in Production example 1 was arranged at the anastomosed site, and the dog was monitored for 16 weeks. Subsequently, the vein was evaluated by diagnosis with Doppler blood flow measurement and color Doppler ultrasound imaging diagnostic unit. The beagle dog was euthanized and the vein at the shunt construction was removed. The smooth muscle layer and elastic fiber layer containing collagen fibers of the removed vein were observed, their thickness was measured, and remodeling to a buffer system vessel was evaluated. The results are shown in Table 2. The results of the evaluation based on the above criteria (a) to (e) were good.

Comparative Example 1

A shunt was constructed in the neck of a beagle dog by anastomosing an artery and vein, and the blood vessel cover was placed on the outer circumference of the vein so that the first end of the blood vessel cover obtained in Production example 4 was arranged at the anastomosed site, and the dog was monitored for 16 weeks. Subsequently, the vein was evaluated by diagnosis with Doppler blood flow measurement and color Doppler ultrasound imaging diagnostic unit. The beagle dog was euthanized and the vein at the shunt construction was removed. The smooth muscle layer and elastic fiber layer containing collagen fibers of the removed vein were observed, their thickness was measured, and remodeling to a buffer system vessel was evaluated. The results are shown in Table 2. The results of the evaluation based on the above criteria (a) to (e) were bad.

TABLE 2

| | Blood vessel cover | 20% elastic index (N) | 50% elastic index (N) | Anastomosis structure | Evaluation |
|---|---|---|---|---|---|
| Example 1 | Production example 1 | 0.73 | 1.07 | arteriovenous | good |
| Comparative example 1 | Production example 4 | 1.48 | 3.4 | arteriovenous | bad |

DESCRIPTION OF REFERENCE SIGNS

1: shunt construction
2: arm
3: artery
4: vein

5: artificial blood vessel
6: anastomosis site
10: blood vessel cover
10*a*: first end of the blood vessel cover
10*b*: second end of the blood vessel cover
10*c*: midpoint of the blood vessel cover
11: first part
12: second part
100*a*: first end part
100*b*: second end part
100*c*: middle part
100: cylindrical sample
101: first pin
102: second pin
L1: distance between peaks in first end part
L2: distance between peaks in second part
x: axial direction
y: radial direction

The invention claimed is:

1. A cylindrical blood vessel cover that is continuous around the entire circumference and to be placed on an outer circumference of a vein that is anastomosed to an artery or to an artificial vessel, comprising a portion (A), wherein
   the portion (A) has a 20% elastic index of 1.2 N or less when an inner diameter of the blood vessel cover is expanded in a radial direction by 20% from its natural state, and
   the 20% elastic index is measured by
   preparing a cylindrical sample that has a length of 5 mm in an axial direction and is continuous around the entire circumference over the entire axial direction by cutting the blood vessel cover perpendicular to the axial direction along a circumferential cut line of the blood vessel cover;
   inserting a first pin and a second pin each having a diameter d of 0.75 mm into a lumen of the cylindrical sample so that each of the first pin and the second pin is parallel to the axial direction of the cylindrical sample;
   fixing the first pin;
   pulling the second pin towards outside of a radial direction of the cylindrical sample;
   measuring a pulling force $F_{1.2}$ when $\pi d+2L$ becomes 1.2 times a perimeter of the cylindrical sample in its natural state given that a distance between the first pin and the second pin is L; and
   dividing the pulling force $F_{1.2}$ by a strain [(1.2−1.0)/1.0] to obtain the 20% elastic index.
2. The blood vessel cover according to claim 1, wherein the 20% elastic index of the portion (A) is 0.1 mN or more.
3. The blood vessel cover according to claim 1, wherein in the axial direction, the blood vessel cover has a first end and a second end; and the blood vessel cover has a first part from the first end to a midpoint between the first end and the second end, and a second part from the midpoint to the second end; and the portion (A) is located in the first part.

4. The blood vessel cover according to claim 3, wherein the blood vessel cover has a first end part from the first end to a midpoint of the first part in the axial direction, and the portion (A) is located in the first end part.

5. The blood vessel cover according to claim 1, wherein the entire blood vessel cover is the portion (A).

6. The blood vessel cover according to claim 1, wherein in the axial direction, the blood vessel cover has a first end and a second end; and the blood vessel cover has a first part from the first end to a midpoint between the first end and the second end, and a second part from the midpoint to the second end; and the 20% elastic index in the second part is smaller than the 20% elastic index in the first part.

7. The blood vessel cover according to claim 1, wherein in the axial direction, the blood vessel cover has a first end and a second end; and the blood vessel cover has a first part from the first end to a midpoint between the first end and the second end, a second part from the midpoint to the second end, a first end part from the first end to a midpoint of the first part, a middle part from the midpoint of the first part to a midpoint of the second part, and a second end part from the midpoint of the second part to the second end; and the blood vessel cover satisfies the relationship Ea>Ec>Eb given that the 20% elastic index in the first end part is Ea, the 20% elastic index in the middle part is Ec, and the 20% elastic index in the second end part is Eb.

8. The blood vessel cover according to claim 1, a length of the portion (A) in the axial direction is 50% or longer of an outer diameter of the artery or artificial vessel to which the vein is anastomosed.

9. The blood vessel cover according to claim 1, wherein an inner diameter of the blood vessel cover is expandable by at least 100% in the radial direction from its natural state throughout the axial direction.

10. The blood vessel cover according to claim 1, having a length in the axial direction of 5 mm or longer.

11. The blood vessel cover according to claim 1, comprising at least one of knitted fabric, woven fabric, and nonwoven fabric as a partial or whole component.

12. The blood vessel cover according to claim 1, having a bellows structure with periodically repeating peaks and valleys in the axial direction, wherein in the axial direction, the blood vessel cover has a first end and a second end; and the blood vessel cover has a first part from the first end to a midpoint between the first end and the second end, a second part from the midpoint to the second end, and a first end part from the first end to a midpoint of the first part; and in the axial direction, a distance between adjacent peaks in the second part is longer than a distance between adjacent peaks in the first end part.

* * * * *